United States Patent [19]

Correa et al.

[11] Patent Number: 5,463,106
[45] Date of Patent: Oct. 31, 1995

[54] PROCESS FOR THE ENANTIOSELECTIVE PREPARATION OF PHENYLISOSRINE DERIVATIVES

[75] Inventors: Arlene G. Correa, Grenoble; Jean-Noel Denis; Andrew E. Greene, both of Uriage, all of France

[73] Assignee: Centre National de la Recherche Scientifique, Paris, France

[21] Appl. No.: 208,751

[22] Filed: Mar. 9, 1994

Related U.S. Application Data

[62] Division of Ser. No. 5,199, Jan. 15, 1993, Pat. No. 5,304, 670, which is a continuation of Ser. No. 803,725, Dec. 9, 1991, abandoned, which is a continuation of Ser. No. 569,442, Aug. 20, 1990, abandoned.

[30] Foreign Application Priority Data

Aug. 23, 1989 [FR] France .................... 89 11162
Oct. 2, 1989 [FR] France .................... 89 12825

[51] Int. Cl.[6] .................... C07C 227/04; C07C 229/34
[52] U.S. Cl. .................... 560/39
[58] Field of Search .................... 560/39

[56] References Cited

U.S. PATENT DOCUMENTS 4,924,012  5/1990  Colin et al. .................... 549/510

Primary Examiner—José G. Dees
Assistant Examiner—Barbara S. Frazier
Attorney, Agent, or Firm—Morgan & Finnegan

[57] ABSTRACT

Process for the enantioselective preparation of phenylisoserine derivatives of general formula (I), in which R represents a phenyl or tert-butoxy radical, $R_1$ represents a hydrogen atom or an alkyl radical containing 1 to 4 carbon atoms and $R_2$ represents a hydrogen atom or a group protecting the alcohol function.

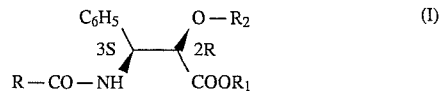

6 Claims, No Drawings

PROCESS FOR THE ENANTIOSELECTIVE PREPARATION OF PHENYLISOSRINE DERIVATIVES

This is a divisional of application Ser. No. 08/005,199 filed on Jan. 15, 1993, now U.S. Pat. No. 5,304,670, which is a continuation application of application Ser. No. 07/803,725 filed Dec. 9, 1991, now abandoned which is a continuation application of Ser. No. 07/569,442 filed Aug. 20, 1990, now abandoned.

The present invention relates to a process for the enantioselective preparation of phenylisoserine derivatives of general formula:

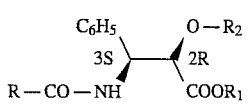

in which R represents a phenyl or tert-butoxy radical, $R_1$ represents a hydrogen atom or an alkyl radical containing 1 to 4 carbon atoms and $R_2$ represents a hydrogen atom or a group protecting the hydroxyl function.

In the general formula (I), $R_2$ represents, more especially, a hydrogen atom or a methoxymethyl radical, 1-ethoxyethyl, benzyloxymethyl, (β-trimethylsilylethoxy)methyl, tetrahydropyrannyl or 2,2,2-trichloroethoxycarbonyl radical. Preferably, the radical $R_2$ is a 1-ethoxyethyl radical.

The product of general formula (I) are useful for preparing derivatives of baccatine III and of 10-deacetylbaccatine III of general formula:

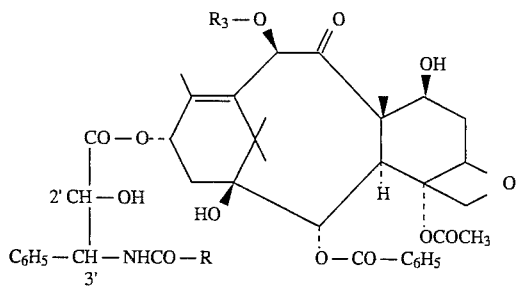

in which $R_3$ represents a hydrogen atom or an acetyl radical and R represents a phenyl radical or a tert-butoxy radical.

The products of general formula (II) in which R represents a phenyl radical correspond to taxol and to 10-deacetyltaxol, and the products of general formula (II) in which R represents a tert-butoxy radical correspond to those which are described in European Patent EP 253,738.

The products of general formula (II), and especially those which occur in the 2'R,3'S form, possess especially advantageous antitumour and antileukaemic properties.

The products of general formula (II) may be obtained by the action of a product of general formula (I) in which $R_1$ represents a hydrogen atom on a taxane derivative of general formula:

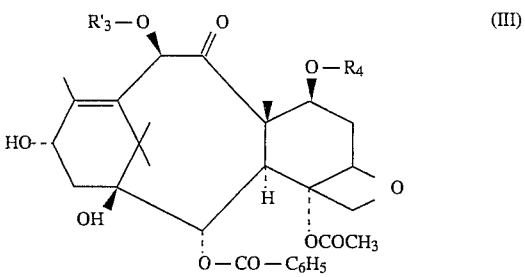

in which $R'_3$ represents an acetyl radical or a group protecting the hydroxyl function and $R_4$ represents a group protecting the hydroxyl function, followed by replacement of the protective groups $R_2$ and $R_4$ and, where appropriate, $R_3$ by a hydrogen atom, under the conditions described by J.-N. DENIS et al., J. Amer. Chem. Soc., 110 (17) 5917–5919 (1988) or by L. MANGATAL et al., Tetrahedron, 45, 4177–4190 (1989).

According to the present invention, the products of general formula (I) in which R represents a phenyl or tert-butoxy radical, $R_1$ represents an alkyl radical containing 1 to 4 carbon atoms and $R_2$ represents a group protecting the hydroxyl function are obtained from an oxirane derivative of general formula:

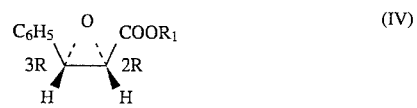

in which $R_1$ is defined as above, which is treated with an azide to give a product of general formula:

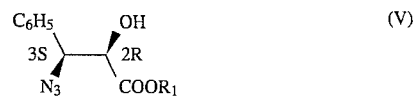

in which $R_1$ is defined as above, the hydroxyl function of which is then protected by a group $R_2$ so as to obtain a product of general formula:

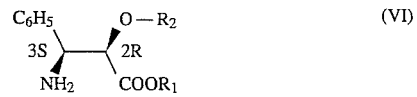

in which $R_1$ is defined as above and $R_2$ represents a group protecting the hydroxyl function, which is reduced to a product of general formula:

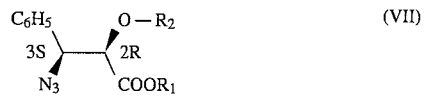

in which $R_1$ and $R_2$ are defined as above, which is treated with a reagent enabling a benzoyl or tertbutoxycarbonyl group to be introduced, to obtain a product of general formula (I) in which $R_1$ represents an alkyl radical containing 1 to 4 carbon atoms, which is then saponified to give a product of general formula (I) in which $R_1$ represents a hydrogen atom.

The opening of the oxirane of general formula (IV) to a product of general formula (V) may be performed by the action of an azide, working in a suitable organic solvent at a temperature generally of between 40° and 80° C. It is advantageous to use trimethylsilyl azide in the presence of zinc chloride, or an alkali metal (sodium, potassium, lithium) azide in an aqueous-methanolic medium in the presence of methyl formate.

The products of general formula (VI) may be obtained from the product of general formula (V) under the usual conditions for preparing ethers and acetals, and more especially according to the processes described by J-N. DENIS et al., J. Org. Chem., 51, 46–50 (1986).

The product of general formula (VII) may be obtained by reduction of the product of general formula (VI) by means of hydrogen in the presence of a hydrogenation catalyst such as palladium on charcoal, working in an alcohol such as methanol.

The product of general formula (I) in which $R_1$ represents an alkyl radical containing 1 to 4 carbon atoms may be obtained by the action of di-tert-butyl dicarbonate or benzoyl chloride on the product of general formula (VII).

In general, the reaction is performed in an organic solvent such as methylene chloride in the presence of an inorganic base such as sodium bicarbonate or an organic base such as a tertiary amine, for example triethylamine. It is not necessary to isolate the product of general formula (VII) in order to react it with di-tert-butyl dicarbonate or benzoyl chloride.

The oxirane derivative of general formula (IV) may be obtained under the conditions described by J-N. DENIS et al., J. Org. Chem., 51, 46–50 (1986).

According to the present invention, the products of general formula (I) in which $R_1$ represents an alkyl radical containing 1 to 4 carbon atoms and $R_2$ represents a hydrogen atom may be obtained by the acylation/hydrogenation of a hydroxy azide of general formula (V) in which $R_1$ is defined as above.

The acylation and hydrogenation may be carried out simultaneously or successively without isolation of the intermediate reaction products.

When R represents a phenyl radical or a tert-butoxy radical, the reaction may be carried out using benzoic anhydride or di-tert-butyl dicarbonate in the presence of hydrogen and a hydrogenation catalyst such as palladium on charcoal, working in an inert organic solvent such as an ester, for example methyl acetate or ethyl acetate, at a temperature of between 0° and 40° C., and preferably in the region of 20° C.

When R represents a phenyl radical, the reaction may be carried out using benzoyl chloride in the presence of an organic base such as triethylamine and an activating agent such as 4-dimethylaminopyridine, then adding methanol and thereafter placing the reaction mixture under a hydrogen atmosphere in the presence of a hydrogenation catalyst such as palladium on charcoal, working in an inert organic solvent such as an ester, for example methyl acetate or ethyl acetate, at a temperature of between 0° and 40° C., and preferably in the region of 20° C.

The products of general formula (I) in which $R_1$ represents an alkyl radical containing 1 to 4 carbon atoms and $R_2$ represents a group protecting the hydroxyl function may be obtained from a product of general formula (I) in which $R_1$ represents an alkyl radical containing 1 to 4 carbon atoms and $R_2$ represents a hydrogen atom, under the usual conditions for preparing the ethers and acetals mentioned above.

The product of general formula (I) in which $R_1$ represents a hydrogen atom may be obtained by the saponification of a product of general formula (I) in which $R_1$ represents an alkyl radical, by means of an inorganic base such as an alkali metal (lithium, sodium) hydroxide, an alkali metal carbonate or bicarbonate (sodium bicarbonate, potassium carbonate or bicarbonate) in an aqueous-alcoholic medium such as a methanol/water mixture at a temperature of between 10° and 40° C., and preferably in the region of 25° C.

The present invention also relates to the preparation of the product of general formula (II), by the condensation of a phenylisoserine derivative of general formula (I) in which $R_1$ represents a hydrogen atom and $R_2$ represents a group protecting the hydroxyl function, when it is obtained by the process according to the present invention, with a product of general formula (III) in which the protective groups represented by $R'_3$ and $R_4$ are generally 2,2,2-trichloroethoxycarbonyl groups or trialkylsilyl radicals in which each alkyl portion contains 1 to 3 carbon atoms, followed by the replacement of the protective groups by a hydrogen atom.

In general, the esterification is performed in the presence of a condensing agent such as a carbodiimide, for example dicyclohexylcarbodiimide, or a reactive carbonate, for example 2-dipyridyl carbonate, and an activating agent such as a dialkylaminopyridine, for example 4-dimethylaminopyridine, working in an aromatic organic solvent such as benzene, toluene, xylenes, ethylbenzene, isopropylbenzene or chlorobenzene at a temperature of between 60° and 90° C.

It is especially advantageous to use a molar excess of acid of general formula (I) relative to the taxane derivative of general formula (III), the condensing agent being used in a stoichiometric amount relative to the acid of general formula (I) and 4-dimethylaminopyridine being used in a stoichiometric amount relative to the taxane derivative of general formula (III).

The replacement of the protective groups by a hydrogen atom may be performed by means of zinc in the presence of acetic acid at a temperature of between 30° and 60° C., or by treatment by means of an inorganic or organic acid such as hydrochloric acid or acetic acid, in solution in an aliphatic alcohol containing 1 to 3 carbon atoms, in the presence of zinc.

The examples which follow, given without implied limitation, show how the invention may be put into practice.

EXAMPLE 1

530 mg of (+)-(methyl 3-azido-2-hydroxy-3-phenylpropionate) (2.4 mmol), 12 cm³ of dry dichloromethane, 60.2 mg of pyridinium p-toluenesulphonate (0.24 mmol) and 2.3 cm³ of ethyl vinyl ether (24 mmol) are introduced successively under an argon atmosphere into a 25-cm³ round-bottomed flask equipped with a magnetic stirrer. The mixture is stirred for 4 hours at a temperature in the region of 20° C. When the reaction is complete, one drop of pyridine is added and 50 cm³ of dichloromethane are then added. The reaction mixture is washed twice with 5 cm³ of water and twice with 5 cm³ of saturated aqueous sodium chloride solution, then dried over anhydrous sodium sulphate. After filtration and evaporation of the solvent, 706 mg of methyl 3-azido-2-(1-ethoxyethoxy)-3-phenylpropionate are obtained in the form of an equimolecular mixture of the 2 epimers.

0.6 g of methyl 3-azido-2-(1-ethoxyethoxy)-3-phenylpropionate (2.05 mmol), 16.4 cm³ of methanol, 0.714 cm³ of triethylamine (5.12 mmol) and 107 mg of palladium on charcoal containing 10% by weight of palladium are introduced successively under an argon atmosphere into a 25-cm³ round-bottomed flask equipped with a magnetic stirrer. The mixture obtained is placed under a hydrogen atmosphere and then stirred vigorously for 4 hours at a temperature in the region of 20° C. When the reaction is complete, the reaction mixture is placed under an argon atmosphere. The catalyst is separated by filtration through Celite. The catalyst is washed three times with 15 cm³ of methylene chloride. The combined organic phases are concentrated to dryness under reduced pressure. A colourless liquid residue is obtained.

The residue obtained above and 10.3 cm³ of dichloromethane are introduced under an argon atmosphere into a 25-cm³ round-bottomed flask equipped with a magnetic stirrer. 1.43 cm³ of triethylamine (10.25 mmol) and 536.9 mg of di-t-butyl dicarbonate (2.46 mmol) are added to the solution obtained. The reaction mixture is stirred for 43 hours at a temperature in the region of 20° C. and 100 cm³ of ethyl acetate are then added. The reaction mixture is washed twice with 10 cm³ of saturated aqueous sodium bicarbonate solution, 3 times with 5 cm³ of water and once with 5 cm³ of saturated aqueous sodium chloride solution, then dried over anhydrous sodium sulphate. After filtration and evaporation of the solvents, a residue (720 mg) is obtained, which is purified by filtration on a column of silica gel, eluting with an ethyl ether/methylene chloride mixture (1:99 by volume). 413 mg of pure methyl (2R,3S)-3-t-butoxy-carbonylamino- 2-(1-ethoxyethoxy)-3-phenylpropionate are thereby obtained in the form of an equimolecular mixture of the 2 epimers.

The overall yield is 55 % from the (+)-(methyl 3-azido-2-hydroxy-3-phenylpropionate).

The characteristics are as follows:

Optical rotation: $[\alpha]_D^{24}=+6.0°$ (c=1.52; chloroform).

Melting point: 105°–109° C.

Infrared spectrum (film): 3350, 3000, 2950, 2900, 2875, 1722, 1665, 1515, 1420, 1380, 1355, 1320, 1305, 1280, 1250, 1240, 1160, 1130, 1100, 1070, 1035, 1020, 995, 945, 890, 860, 840, 760, 745 and 698 cm⁻¹.

Proton nuclear magnetic resonance spectrum (300 MHz, CDCl₃, chemical shifts in ppm, coupling constants J in Hz): 0.79 and 0.96 (2t, J=7.0, 3H); 1.08 and 1.16 (2d, J=5.4, 3H); 1.41 (s broad, 9H); 2.69–2.75 and 3.14–3.34 (m, 2H); 3.757 and 3.762 (2s, 3H); 4.34 and 4.46 (2s broad, 1H); 4.39 and 4.73 (2q, J=5.4, 1H); 5.22 and 5.54 (2s broad, 1H); 7.23–7.33 (m, 5H aromatic).

Mass spectrum (c.i., NH₃+isobutane): m/e=385 (MH+NH₃)⁺, 368 (MH)³⁰, 339, 322, 296, 283, 257, 240, 222, 206.

Elemental analysis: C % calculated 62.10 found 62.01 H % calculated 7.96 found 7.97.

(+)-(Methyl 3-azido-2-hydroxy-3-phenylpropionate) may be prepared according to one of the following methods:

a) 84 mg of methyl (2R,3R)-3-phenyloxiranecarboxylate (0.472 mmol), 65.1 mg of trimethylsilyl azide (0.57 mmol) and 2–3 mg of zinc chloride are introduced under an argon atmosphere into a 5-cm³ round-bottomed flask equipped with a magnetic stirrer and surmounted by a condenser. The reaction mixture is heated for 20 hours to 72° C. 0.47 cm³ of a solution prepared from 2 cm³ of tetrahydrofuran, 0.2 cm³ of acetic acid and two drops of concentrated hydrochloric acid is added. Hydrolysis is complete after one hours' reaction at a temperature in the region of 20° C. 20 cm₃ of dichloromethane and 3 cm³ of water are added to the reaction mixture. The two phases are separated after settling has taken place.

The aqueous phase is extracted twice with 5 cm³ of dichloromethane. The combined organic phases are washed twice with 5 cm³ of saturated aqueous sodium bicarbonate solution, three times with 5 cm³ of water and once with 5 cm³ of saturated aqueous sodium chloride solution, and are then dried over anhydrous sodium sulphate. After filtration and evaporation of the solvents under reduced pressure, a residue (97 mg) is obtained, which is purified by filtration on a column of silica gel, eluting with an ether/hexane mixture (2:8 by volume). 91 mg of (+)-(methyl 3-azido-2-hydroxy-3-phenylpropionate) are thereby obtained in an 87% yield.

b) 430 mg of methyl (2R,3R)-3-phenyloxiranecarboxylate (2.4 mmol), 12 cm³ of a methanol/water mixture (8:1 by volume), 800 mg of sodium azide (12.3 mmol) and then 2 cm³ of methyl formate (3.3 mmol) are introduced successively under an argon atmosphere into a 50-cm₃ round-bottomed flask equipped with a magnetic stirrer and surmounted by a condenser. The reaction mixture is heated to 50° C. and then stirred for 24 hours. After cooling to a temperature in the region of 20° C., the reaction mixture is diluted by adding 50 cm³ of ether, and 5 cm³ of water are then added. The two phases are separated after settling has taken place. The aqueous phase is extracted twice with 10 cm³ of ethyl ether. The combined organic phases are washed with 5 cm³ of saturated aqueous sodium chloride solution and then dried over anhydrous sodium sulphate. After filtration and concentration under reduced pressure, a residue is obtained, which is purified by filtration on silica gel, eluting with an ethyl acetate/hexane mixture (2:8 by volume). 475 mg of pure (+)-(methyl 3-azido-2-hydroxy- 3-phenylpropionate) are obtained in a 90% yield.

The product obtained possesses characteristics (infrared spectrum, proton nuclear magnetic resonance spectrum) identical to those described by J-N. DENIS et al., J. Org. Chem., 51, 46–50 (1986).

Melting point=56°–57° C. (pentane); $[\alpha]_D^{24}=+142°$ (c=1.1; chloroform).

EXAMPLE 2

146.8 mg of methyl (2R,3S)-3-t-butoxycarbonylamino- 2-(1-ethoxyethoxy)-3-phenylpropionate (0.4 mmol), 14 cm³ of distilled methanol, 7 cm³ of water and 166 mg of solid potassium carbonate (1.2 mmol) are introduced successively into a 50-cm³ round-bottomed flask equipped with a magnetic stirrer. The mixture is stirred for 40 hours at a temperature in the region of 20° C. and the methanol is then evaporated off under reduced pressure. The residual basic aqueous phase is washed several times with ether, then acidified with 2.5% (weight/volume) aqueous hydrochloric acid solution in the presence of methylene chloride and then extracted four times with 20 cm³ of methylene chloride. The combined organic phases are washed 4 times with 5 cm³ of water and then once with 5 cm³ of saturated sodium chloride solution, and then dried over anhydrous magnesium sulphate. After filtration and evaporation of the solvents under reduced pressure, 108 mg of pure (2R,3S)-3-t-butoxycarbonylamino- 2-(1-ethoxyethoxy)-3-phenylpropionic acid are obtained in a 76% yield.

The characteristics are as follows:

Deliquescent product.

Optical rotation: $[\alpha]_D^{24}=+17°$ (c=1.28; chloroform).

Infrared spectrum (film): main characteristic absorption bands at: 3700–2200, 3060, 2980, 2930, 1720, 1660, 1602, 1590, 1500, 1450, 1400, 1370, 1280, 1250, 1170, 1080, 1050, 1030, 955, 930, 890 and 700 cm⁻¹.

Proton nuclear magnetic resonance spectrum (300 MHz, CDCl₁, chemical shifts in ppm, coupling constants J in Hz):

0.81 and 1.04 (2t, J=7, 3H); 1.18 and 1.20 (2d, J=5.4, 3H); 1.42 (s, 9H); 2.60–2.88 and 3.15–3.52 (m, 2H); 4.35–4.50 and 4.65–4.80 (m, 2H); 5.29 (s broad, 1H); 5.72 (s broad, 1H); 7.13–7.38 (m, 5H aromatic); 8.52 (s broad, 1H).

EXAMPLE 3

A mixture of 1.51 g (6.83 mmol) of (+)-[methyl (2R,3S)-3-azido-2-hydroxy-3-phenylpropionate ], 1.93 g (13.7 mmol) of benzoyl chloride, 2.07 g (20.4 mmol) of triethylamine and 30.2 mg (0.25 mmol) of 4-dimethylaminopyridine in 27 cm$^3$ of ethyl acetate is stirred under an argon atmosphere at 20° C. for 4 hours, and 1.4 cm$^3$ of methanol are then added. The mixture is stirred for a further 3 hours, 152 mg of palladium on charcoal containing 10% (w/w) of palladium are then added and the mixture is placed under a hydrogen atmosphere. It is stirred for 68 hours. The hydrogen is replaced by argon, the reaction mixture is diluted in 100 cm$^3$ of methylene chloride and the palladium on charcoal is removed by filtration under vacuum through Celite. The solids are washed 3 times with 20 to 30 cm$^3$ of methylene chloride and the solvents are then removed under vacuum. A crude product is obtained, which is purified by chromatography on silica gel, eluting with an ether/dichloromethane mixture (5:95 by volume). 1.88 g of (−)-(2R,3S)-N-benzoyl-3-phenylisoserine methyl ester are thereby obtained, the characteristics of which are as follows:

Melting point: 184°–185° C. (methylene chloride/cyclohexane)

Optical rotation: $[\alpha]_D^{24}$=−48 (c=1; methanol). The yield is 92%.

(+)-[Methyl (2R,3S)-3-azido-2-hydroxy-3phenylpropionate] may be prepared in the following manner:

1.35 g (7.58 mmol) of (+)-[methyl (2R,3R)-3-phenyloxiranecarboxylate], dissolved in 40 cm$^3$ of a methanol/water mixture (8:1 by volume), is treated with 6.3 cm$^3$ of methyl formate and 2.46 g (37.8 mmol) of sodium azide. The mixture is stirred for 46 hours at 50° C. under an argon atmosphere. The product obtained is extracted with ether under the usual conditions. The crude product obtained is purified by chromatography on silica gel, eluting with hexane containing 10% of ethyl acetate. 1.59 g of (+)-[methyl (2R,3S)-3-azido-2-hydroxy- 3-phenylpropionate] are thereby obtained, the characteristics of which are as follows:

Melting point: 56°–57° C. (pentane)

Optical rotation: $[\alpha]_D^{24}$=+142° (c=1.1; chloroform). The yield is 95%.

EXAMPLE 4

A suspension of 148 mg of palladium on charcoal containing 10% (w/w) of palladium in 3 cm$^3$ of ethyl acetate is stirred for 10 minutes under a hydrogen atmosphere at 20° C., and a solution of 1.75 g (8.02 mmol) of di-tert-butyl dicarbonate and 1.48 g (6.70 mmol) of (+)-[methyl (2R,3S)-3-azido-2-hydroxy-3phenylpropionate] in 12 cm$^3$ of ethyl acetate is then added.

The mixture is stirred for 56 hours. The hydrogen is replaced by argon, the mixture is diluted in 100 cm$^3$ of ethyl acetate and the palladium on charcoal is removed by filtration under vacuum through Celite. The solids are washed 3 times with 30 to 40 cm$^3$ of ethyl acetate and the solvent is removed under vacuum. The crude product is obtained, which is purified by chromatography on silica gel, eluting with an ether/dichloromethane mixture (5:95 by volume). 1.81 g of (−)-(2R,3S)-N-(tert-butoxycarbonyl)-3-phenylisoserine methyl ester are thereby obtained, the characteristics of which are as follows:

Melting point: 130.5°–131.5° C. (methylene chloride/cyclohexane)

Optional rotation: $[\alpha]_D^{24}$=−7° (c=1.2; chloroform).

Infrared spectrum: main characteristic absorption bands at 3500, 3380, 3110, 3060, 3000, 2975, 2930, 1735, 1690, 1518, 1500, 1442, 1390, 1360, 1300, 1250, 1170, 1100, 1050, 1030, 980, 940, 930, 900 and 705 cm$^{-1}$.

Proton nuclear magnetic resonance spectrum (chemical shifts in ppm, coupling constants J in Hz): 1.42 (s broad, 9H); 3.11 (s broad, 1H); 3.84 (s, 3H); 4.47 (s broad, 1H); 5.21 (distorted d, J=9.4, 1H); 5.36 (distorted d, J=8.5, 1H); 7.26–7.37 (m, 5H).

Mass spectrum (c.i., NH$_3$+isobutane): m/e=313 (MH+NH$_3$)$^+$, 296 (MH)$^+$, 257, 240, 206, 196.

Elemental analysis: C % calculated 61.00 found 60.85 H % calculated 7.17 found 7.17. The yield is 92%.

We claim:

1. Process for the enantioselective preparation of phenylisoserine of formula:

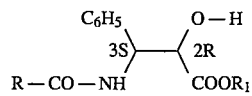

in which R represents a t-butoxy radical and $R_1$ represents an alkyl radical containing 1 to 4 carbon atoms comprising, reacting di-tert-butyl dicarbonate and hydrogen with a hydroxy azide of formula:

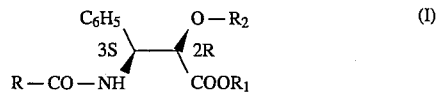

in which $R_1$ represents a $C_1$–$C_4$ alkyl radical, in the presence of an organic base and an activating agent, at a temperature of between 0° and 40° C., without isolation of the intermediate reaction products.

2. Process according to claim 1, wherein the hydrogenation of the hydroxy azide is performed in the presence of a hydrogenation catalyst in a lower alcohol.

3. Process according to claim 1, wherein the reaction is carried out in the presence of an inert organic solvent is selected from the group consisting of halogenated hydrocarbons and the base is triethylamine.

4. Process according to claim 1, wherein the reaction is carried out in the presence of inert organic solvent selected from the group consisting of methyl acetate and ethyl acetate.

5. Process according to claim 1, wherein an inorganic base selected from the group consisting of alkali metal hydroxides, carbonates and bicarbonates in an aqueous-alcoholic medium is added.

6. Process according to claim 3, wherein the organic solvent is methylene chloride.

* * * * *

UNITED STATES PATENT AND TRADEMARK OFFICE
CERTIFICATE OF CORRECTION

PATENT NO. : 5,463,106

DATED : October 31, 1995

INVENTOR(S) : Arlene G. Correa et al.

It is certified that error appears in the above-indentified patent and that said Letters Patent is hereby corrected as shown below:

On the title page, item [54] and column 1, line 2, "PHENYLISOSRINE" should read --PHENYLISOSERINE--.

Claim 1, Column 8, Lines 36-40, formula (I) should read

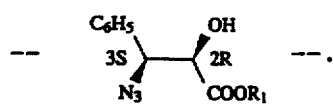

Claim 3, Column 8, Line 49, after "solvent" delete "is".

Claim 4, Column 8, Line 53, before "insert" insert --an--.

Claim 3, Column 8, line 49 and claim 4, column 8, line 53, "inert" should read --insert--.

Signed and Sealed this

Twenty-first Day of January, 1997

Attest:

BRUCE LEHMAN

*Attesting Officer*          *Commissioner of Patents and Trademarks*